US010166336B2

(12) United States Patent
Lumme et al.

(10) Patent No.: US 10,166,336 B2
(45) Date of Patent: Jan. 1, 2019

(54) AUTO-INJECTOR FOR RETRACTABLE PREFILLED SYRINGE

(71) Applicant: UNL Holdings LLC, New York, NY (US)

(72) Inventors: Katlin M. Lumme, Mableton, GA (US); Philip A. Weaver, Denver, PA (US); Joseph Hermes Kaal, Raworth (AU); Christopher Charles Rafferty, Raworth (AU); Craig Stephen Thorley, Largs (AU); Joel M. Ondrejicka, Lewisberry, PA (US)

(73) Assignee: UNL Holdings LLC, New York, NY (US)

( * ) Notice: Subject to any disclaimer, the term of this patent is extended or adjusted under 35 U.S.C. 154(b) by 691 days.

(21) Appl. No.: 14/328,914

(22) Filed: Jul. 11, 2014

(65) Prior Publication Data
US 2014/0323982 A1    Oct. 30, 2014

Related U.S. Application Data

(63) Continuation of application No. 13/593,293, filed on Aug. 3, 2012, now Pat. No. 8,808,244.
(Continued)

(51) Int. Cl.
A61M 5/20    (2006.01)
A61M 5/32    (2006.01)

(52) U.S. Cl.
CPC ........ *A61M 5/2033* (2013.01); *A61M 5/3234* (2013.01); *A61M 2005/2026* (2013.01); *A61M 2005/3231* (2013.01); *Y10T 137/0402* (2015.04)

(58) Field of Classification Search
CPC ................. A61M 5/2033; A61M 2005/2026
(Continued)

(56) References Cited

U.S. PATENT DOCUMENTS 3,395,704 A    8/1968    Frey et al.
5,425,715 A    6/1995    Dalling et al.
(Continued)

FOREIGN PATENT DOCUMENTS

AU    2003275893 B2    6/2004
CN    100553700 C    10/2009
(Continued)

OTHER PUBLICATIONS

European Patent Office, Extended European Search Report in European Patent Application No. 14193283, dated Jan. 8, 2015, 6 pages.
(Continued)

*Primary Examiner* — Edelmira Bosques
(74) *Attorney, Agent, or Firm* — Hamilton, Brook, Smith & Reynolds, P.C.

(57) ABSTRACT

An actuation mechanism for an automatic injector includes a first actuation spring, a first actuation pill, a second actuation spring, and a second actuation pill. In an initial configuration the first actuation spring resides in a compressed, energized state substantially within an upper portion of first actuation pill and the second actuation spring resides in a compressed, energized state between the first actuation pill and the second actuation pill. An automatic injector includes a housing, an activation mechanism, an actuation mechanism, and a syringe cartridge having a plunger and a needle assembly. A retractable syringe may be utilized as a syringe cartridge, such as a prefilled retractable syringe with integrated safety features which retract the needle after use. The automatic injector may be utilized to
(Continued)

inject the needle, deliver a drug treatment, and activate retraction of the needle. Methods of assembly and operation are also provided.

14 Claims, 12 Drawing Sheets

Related U.S. Application Data

(60) Provisional application No. 61/256,995, filed on Aug. 24, 2011.

(58) Field of Classification Search
USPC .......................................................... 604/218
See application file for complete search history.

(56) References Cited

U.S. PATENT DOCUMENTS

| | | |
|---|---|---|
| 6,083,199 A | 7/2000 | Thorley et al. |
| 6,090,070 A | 7/2000 | Hager et al. |
| 6,387,078 B1 | 5/2002 | Gillespie, III |
| 6,607,508 B2 | 8/2003 | Knauer |
| 7,381,201 B2 | 6/2008 | Gilbert et al. |
| 7,500,967 B2 | 3/2009 | Thorley et al. |
| 7,736,353 B2 | 6/2010 | Reynolds |
| 7,744,582 B2 | 6/2010 | Sadowski et al. |
| 7,749,195 B2 | 7/2010 | Hommann |
| 7,935,087 B2 | 5/2011 | Judd et al. |
| 8,002,745 B2 | 8/2011 | Kaal et al. |
| 8,021,333 B2 | 9/2011 | Kaal et al. |
| 8,052,654 B2 | 11/2011 | Kaal et al. |
| 8,114,050 B2 | 2/2012 | Kaal et al. |
| 8,167,937 B2 | 5/2012 | Cerruti et al. |
| 8,366,669 B2 | 2/2013 | Donald et al. |
| 8,702,653 B2 | 4/2014 | Samandi et al. |
| 8,808,244 B2 | 8/2014 | Adlon et al. |
| 2001/0037087 A1 | 11/2001 | Knauer |
| 2002/0177787 A1* | 11/2002 | Duchon ............... A61M 1/3627 600/578 |
| 2005/0080377 A1 | 4/2005 | Sadowski et al. |
| 2005/0277886 A1 | 12/2005 | Hommann et al. |
| 2006/0184137 A1 | 8/2006 | Reynolds |
| 2008/0195056 A1* | 8/2008 | Bishop ................. A61M 5/2033 604/218 |
| 2009/0254048 A1 | 10/2009 | Hetherington |
| 2011/0015572 A1 | 1/2011 | Thorley et al. |
| 2011/0092954 A1 | 4/2011 | Jennings |
| 2012/0056019 A1 | 3/2012 | Renz et al. |

FOREIGN PATENT DOCUMENTS

| | | |
|---|---|---|
| CN | 101730558 A | 6/2010 |
| DE | 20 2009 003009 U1 | 6/2009 |
| EP | 2331171 | 6/2011 |
| FR | 1538565 A | 9/1968 |
| JP | 2007-504867 A | 3/2007 |
| JP | 2008-543500 A | 12/2008 |
| WO | WO 1994/21316 A1 | 9/1994 |
| WO | WO 95/04562 A1 | 2/1995 |
| WO | WO 03/008023 A1 | 1/2003 |
| WO | WO 2004/000395 A1 | 12/2003 |
| WO | WO 2004/047890 A1 | 6/2004 |
| WO | WO 2004/047891 A1 | 6/2004 |
| WO | WO 2005/018721 A1 | 3/2005 |
| WO | WO 2006/108243 A2 | 10/2006 |
| WO | WO 2006/119570 A1 | 11/2006 |
| WO | WO 2007/002052 A2 | 1/2007 |
| WO | WO 2007/036676 A1 | 4/2007 |
| WO | WO 2009/003234 A1 | 1/2009 |
| WO | WO 2009/007229 A1 | 1/2009 |
| WO | WO 2009/063030 A1 | 5/2009 |
| WO | WO 2009/153540 A1 | 12/2009 |
| WO | WO 2009/153543 A1 | 12/2009 |
| WO | WO 2010/049239 A1 | 5/2010 |
| WO | WO 2011/057335 A1 | 5/2011 |
| WO | WO 2011/075760 A1 | 6/2011 |
| WO | WO 2013/028906 A1 | 6/2011 |
| WO | WO 2011/089417 A1 | 7/2011 |
| WO | WO 2011/109205 A1 | 9/2011 |
| WO | WO 2011/137488 A1 | 11/2011 |
| WO | WO 2011/141907 A1 | 11/2011 |
| WO | WO 2012/098371 A1 | 7/2012 |

OTHER PUBLICATIONS

European Patent Office, International Search Report and Written Opinion in International Patent Application No. PCT/US2013/049314, dated Oct. 15, 2013, 11 pages.

European Patent Office, International Search Report in International Application No. PCT/US2012/052129, 5 pages dated (Dec. 11, 2012).

European Patent Office, Written Opinion of the International Searching Authority in International Application No. PCT/US2012/052129, 6 pages dated (Dec. 11, 2012).

European Patent Office, Written Opinion of the International Searching Authority in Application No. PCT/US2013/024819, 8 pages, dated Apr. 16, 2013.

Non-Final Office Action for U.S. Appl. No. 13/593,293, dated Oct. 1, 2013.

Notice of Allowance for U.S. Appl. No. 13/593,293, dated Apr. 17, 2014.

* cited by examiner

AUTO-INJECTOR FOR RETRACTABLE PREFILLED SYRINGE

CROSS-REFERENCE TO RELATED APPLICATIONS

This application is a continuation of U.S. application Ser. No. 13/593,293 filed Aug. 23, 2012, which claims priority to U.S. Provisional Application No. 61/526,995, filed on Aug. 24, 2011, both of which are included by reference herein in their entireties for all purposes.

FIELD

THIS INVENTION relates to automatic injectors for retractable syringes. More particularly, this invention relates to actuation mechanisms for automatic injectors, automatic injectors for retractable syringes, the methods of operating such devices, and the methods of assembling such devices.

BACKGROUND

Manually activated syringes are commercially available from a variety of manufacturers, including the owner and assignee of the present invention, and are used in the administration of drug solutions, drug suspensions, vaccines, medicinal therapies, and any other liquid medicament by parenteral injection. Such syringes are commonly utilized by medical practitioners to administer injections to patients but are difficult to use by self-administering patients.

An auto-injector is an automatic injection device designed to facilitate delivery of a dose of medicament to a patient through a hypodermic needle, the injection usually being administered by the patient themselves. An auto-injector works, for example, by delivering an injection automatically upon activation by the patient. This is in contrast to a conventional manually activated syringe where the patient themselves needs to directly depress a plunger into a barrel containing medicament in order to effect the injection. Auto-injectors have proven particularly useful in allowing the medically untrained user to administer a parenteral injection, and can provide both psychological and physical advantages to patients. Patients needing to inject medication for chronic disease management have used auto-injectors since the first reusable auto injector was introduced in the 1990s. An auto injector provides protection for the primary container, generally a pre-filled syringe, and offers an easy-to-use solution for automatic injection of medication. As used herein, the terms "automatic injector" and "auto-injector" are meant to refer to the same devices.

In addition to automatic needle insertion and dose delivery, some auto-injectors also incorporate safety mechanisms to automatically protect the patient from the needle after use. The automatic injectors of the prior art are usually provided with needle shields which extend over the needle when actuated. However, such safety mechanisms may fail to actuate and/or can be easily reversed, thereby leaving the patient exposed to the needle and susceptible to injury. Additionally, known automatic injectors generally link visual, tactile or audible indicators to the end of plunger stroke or actuation of some safety mechanism, instead of to the end of drug dose. Accordingly, the self-administering patient is not provided with an indication that the drug has been fully delivered and may remove the needle or actuate the safety mechanisms prematurely.

SUMMARY

The present invention provides actuation mechanisms for automatic injectors, automatic injectors for retractable syringes, the methods of operating such devices, and the methods of assembling such devices. The automatic injectors of the present invention provide integrated safety features which automatically retract the needle or cannula into the device to, for example, prevent injuries related to accidental needlestick. Additionally, the embodiments of the present invention provide true end of dose indication to users, informing the user that the drug delivery has completed and that the device is safe for removal and disposal. Accordingly, the novel devices of the present invention alleviate one or more of the problems associated with prior art devices, such as those referred to above.

In a first embodiment, the present invention provides an actuation mechanism for an automatic injector. The actuation mechanism includes a first actuation spring, a first actuation pill, a second actuation spring, and a second actuation pill, wherein in an initial configuration the first actuation spring resides in a compressed, energized state substantially within an upper portion of first actuation pill and the second actuation spring resides in a compressed, energized state between the first actuation pill and the second actuation pill. The first actuation pill and the second actuation pill are detachably connected by engagement between one or more connector prongs of the first actuation pill and one or more respective connection bridges of second actuation pill. The one or more connector prongs of the first actuation pill may each have protrusions which extend outwards from the first actuation pill.

The first actuation pill may have one or more locking hooks at a proximal end of the first actuation pill. Similarly, the second actuation pill may have one or more retention prongs at a distal end of the second actuation pill. Furthermore, the first actuation pill may have one or more guide prongs extending outwards from the first actuation pill. The first actuation pill and second actuation pill are substantially cylindrical and may be made of a number of standard materials, preferably the same or different plastics.

In another embodiment, the present invention provides an automatic injector having a housing, an activation mechanism, an actuation mechanism, and a syringe cartridge having a plunger and a needle assembly. The actuation mechanism may be as described above and have a first actuation spring, a first actuation pill, a second actuation spring, and a second actuation pill, wherein in an initial configuration the first actuation spring resides in a compressed, energized state substantially within an upper portion of first actuation pill and the second actuation spring resides in a compressed, energized state between the first actuation pill and the second actuation pill. The housing may be a single component or may comprise two or more components such as, for example, an upper housing and a lower housing. The upper housing, the lower housing, the first actuation pill, and the second actuation pill may be a myriad of shapes, but are preferably substantially cylindrical.

In at least one embodiment of the present invention, the first actuation pill has one or more locking hooks at a proximal end of the first actuation pill which initially engage a locking plateau at an interior proximal end of the housing. The activation mechanism is capable of engaging the one or more locking hooks of the first actuation pill to disengage the locking hooks from the locking plateau of the housing upon activation by the user. The activation mechanism may include one or more locking grooves within which corresponding locking prongs of the housing may travel. In one configuration of the activation mechanism, the locking prongs may prevent activation of the activation mechanism.

In another configuration of the activation mechanism, however, such as by rotation of the activation mechanism for example, the locking prongs may permit the activation of the activation mechanism.

In a preferred embodiment, the first actuation pill and the second actuation pill reside within the housing and are detachably connected with each other by engagement between one or more connector prongs of the first actuation pill and one or more respective connection bridges of second actuation pill. The one or more connector prongs may each have protrusions which interface with longitudinal channels along an inner surface of the housing. One or more recesses may exist on the inner surface of the housing, wherein, when the protrusions of the connector prongs interface with the recesses, the expansion of the protrusions into the recesses permits the one or more connector prongs of the first actuation pill to disengage from the one or more respective connection bridges of second actuation pill. According, by user action on the activation mechanism, the activation mechanism engages the one or more locking hooks of the first actuation pill to disengage the locking hooks from the locking plateau of the housing. This action permits the first actuation spring to expand, thereby translating the actuation mechanism within the housing in the distal direction along the axis of the automatic injector. As the protrusions reach recesses within the inner surface of the housing, the one or more connector prongs of the first actuation pill are permitted to disengage from the one or more respective connection bridges of second actuation pill. This action permits the second actuation spring to expand, thereby translating the second actuation pill in the distal direction along the axis of the automatic injector. If the syringe cartridge contains a drug treatment, such as in the case of a pre-filled syringe, the function of the actuation mechanism may be utilized to inject a needle and deliver the drug treatment into a patient. Optionally, when a retractable syringe is utilized as a syringe cartridge, the actuation mechanism may further be utilized to activate a retraction mechanism.

In a preferred embodiment of the present invention, the syringe cartridge of the automatic injector is a retractable syringe. Such syringes may further contain safety features which retract the needle after use, providing desirable needle-stick prevention, and prevent re-use of the syringe. Suitably, the plunger is slidably moveable within the barrel of the syringe to thereby facilitate delivery of the drug treatment to a user, patient or other recipient. The retractable syringe may include a retractable needle assembly. Preferably, the plunger is capable of engaging the needle assembly, or a portion thereof, to retract the cannula or needle. Suitably, retraction of the needle is facilitated by a biasing member such as a spring, elastic or other member capable of storing and releasing energy to facilitate needle retraction. It will be appreciated that the retractable syringe may comprise any needle retraction mechanism that is operable with the automatic injector disclosed herein. By way of example, the needle retraction mechanism may be as described in International Publication WO2006/119570, International Publication WO2006/108243, International Publication WO2009/003234 and International Publication WO2011/075760, although without limitation thereto.

According to one embodiment, the retractable syringe comprises: a plunger comprising a biasing member, a plunger inner, a plunger outer and one or more locking members, wherein the plunger inner and plunger outer co-operate to releasably maintain said biasing member in an initially energized state; and a needle assembly comprising the retractable needle, wherein the retractable needle comprises a cannula and a needle body engageable by the plunger inner. Preferably, a plunger seal is mounted to the plunger inner and is capable of engaging said needle body. Preferably, the needle assembly may further comprise a needle seal that retains the retractable needle, wherein the cannula of the retractable needle passes through the needle seal to permit delivery of the mixed substances or mixture to a user, patient, or other recipient.

In at least one embodiment, the syringe further comprises a release ring. Suitably, the release ring is at a proximal end of the syringe barrel and is engageably or connectably coupled, connectable or affixed to the barrel. The release ring may be a separate component or integral with the barrel. The release ring may activate needle retraction after the plunger inner of the retractable syringe has engaged the needle body. Upon activation of needle retraction, the plunger inner and plunger outer disengage allowing the biasing member to expand from its initially energized state. The plunger outer remains substantially in contact or connection with the release ring, while the plunger inner is axially translated in the proximal direction by release of the biasing member to enable retraction of the cannula and needle body.

Suitably, the retractable syringe comprises one or more plunger locking systems. In one embodiment of said locking system, the plunger inner of the plunger comprises a locking member which is capable of engaging the release ring of the syringe after needle retraction to thereby prevent or impede further movement of the plunger inner relative to the release ring. In at least one embodiment of the present invention, the retractable syringe comprises a retraction mechanism essentially as described in WO2011/075760. Additionally or alternatively, the force of the second actuation spring acting upon the plunger outer itself may prevent or "lock-out" the plunger outer from axial travel in the proximal direction after actuation.

In a further embodiment, the present invention provides a method of assembling an automatic injector which includes the steps of: (i) compressing a second actuation spring between a first actuation pill and a second actuation pill and locking the second actuation spring in the compressed, energized state by detachably engaging one or more connector prongs of the first actuation pill with one or more respective connection bridges of second actuation pill; (ii) inserting a first actuation spring into a housing and compressing the first actuation spring between the housing and the first actuation pill by detachably engaging one or more locking hooks of the first actuation pill with a locking plateau of the housing, wherein the first actuation spring is initially maintained in a compressed, energized state substantially within an upper portion of the first actuation pill; and (iii) inserting a syringe cartridge comprising a plunger and a needle assembly into the housing such that a distal end of the plunger contacts the second actuation pill. The method may further comprise the step of: attaching an activation mechanism to the housing, wherein the activation mechanism is configured to contact the one or more locking hooks of the first actuation pill upon activation.

In a further embodiment, the present invention provides a method of operating an automatic injector which includes the steps of: (i) disengaging one or more locking hooks of a first actuation pill from a locking plateau of a housing, wherein such disengagement permits a first actuation spring to expand substantially along a longitudinal axis of the housing from its initial energized state; (ii) disengaging one or more connector prongs of the first actuation pill from corresponding connection bridges of a second actuation pill, wherein such disengagement permits a second actuation spring to expand substantially along the longitudinal axis of the housing from its initial energized state; and (iii) activating a retraction mechanism of a syringe cartridge comprising a plunger and a needle assembly, wherein the needle assembly comprises a retractable needle having a cannula and a needle body, to retract the retractable needle. The method may further include the steps of: operating the plunger of the automatic injector to deliver a substance to a recipient. Prior to step (i), the method may further include the step of: unlocking an activation mechanism and activating the activation mechanism.

Throughout this specification, unless otherwise indicated, "comprise," "comprises," and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings wherein:

FIG. 1B shows an isometric view of the interior components of the automatic injector shown in FIG. 1a;

DETAILED DESCRIPTION

Figure 1A:
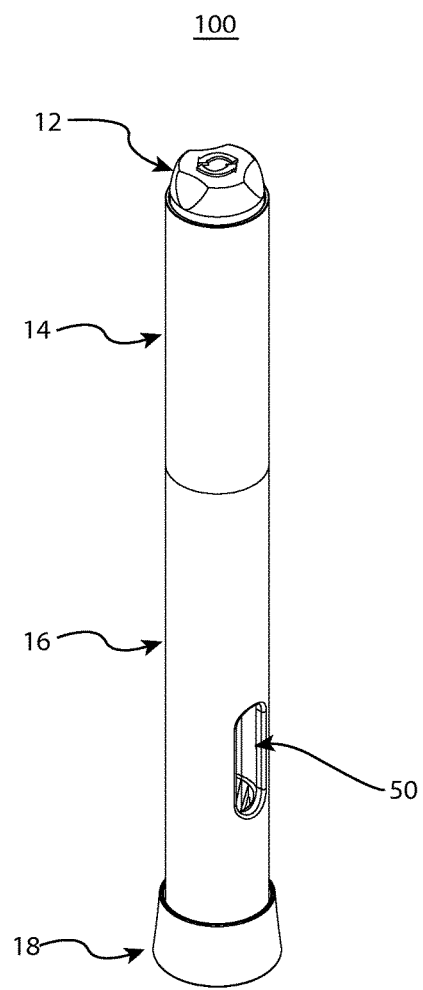
FIG. 1A shows an isometric view of an automatic injector, according to one embodiment of the present invention.

The novel devices of the present invention provide integrated safety features which automatically retract the needle or cannula into the device and provide true end of dose indication to users. Such devices are safe and easy to use, and are aesthetically and ergonomically appealing for self-administering patients. The devices described herein incorporate features which make activation, operation, and lockout of the device simple for even untrained users. The novel devices of the present invention provide these desirable features without any of the problems associated with known prior art devices.

As used herein to describe the actuation mechanisms, automatic injectors, syringe cartridges, or any of the relative positions of the components of the present invention, the terms "axial" or "axially" refer generally to a longitudinal axis "A" around which the actuation mechanisms and automatic injectors are preferably positioned, although not necessarily symmetrically there-around. The term "radial" refers generally to a direction normal to axis A. The terms "proximal," "rear," "rearward," "back," or "backward" refer generally to an axial direction in the direction "P" of the plunger. The terms "distal," "front," "frontward," "depressed," or "forward" refer generally to an axial direction in the direction "D" of the needle. As used herein, the term "glass" should be understood to include other similarly non-reactive materials suitable for use in a pharmaceutical grade application that would normally require glass. The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" does not include either glass or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration. "Fluid" refers primarily to liquids, but can also include suspensions of solids dispersed in liquids, and gasses dissolved in or otherwise present together within liquids inside the fluid-containing portions of syringes. The term "spring" is used herein with reference to one or more "biasing members," and any type of spring or other biasing member may be utilized within the inventions herein.

Figure 1B:
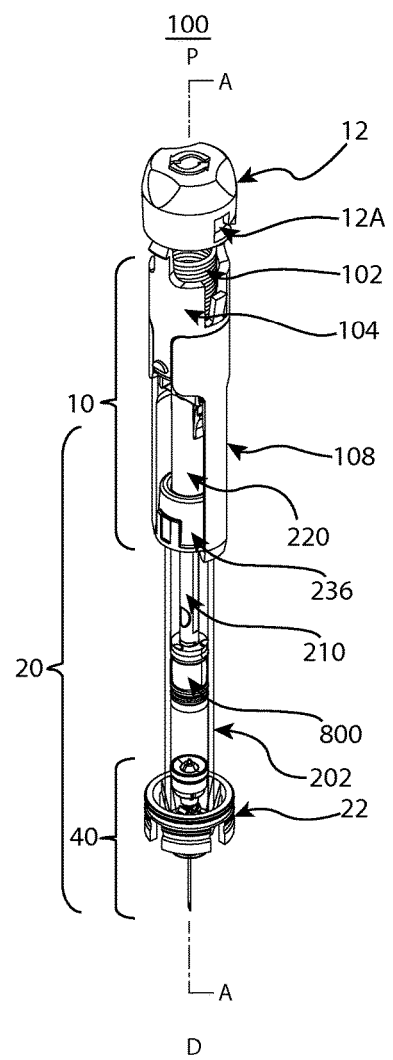
Figure 2:
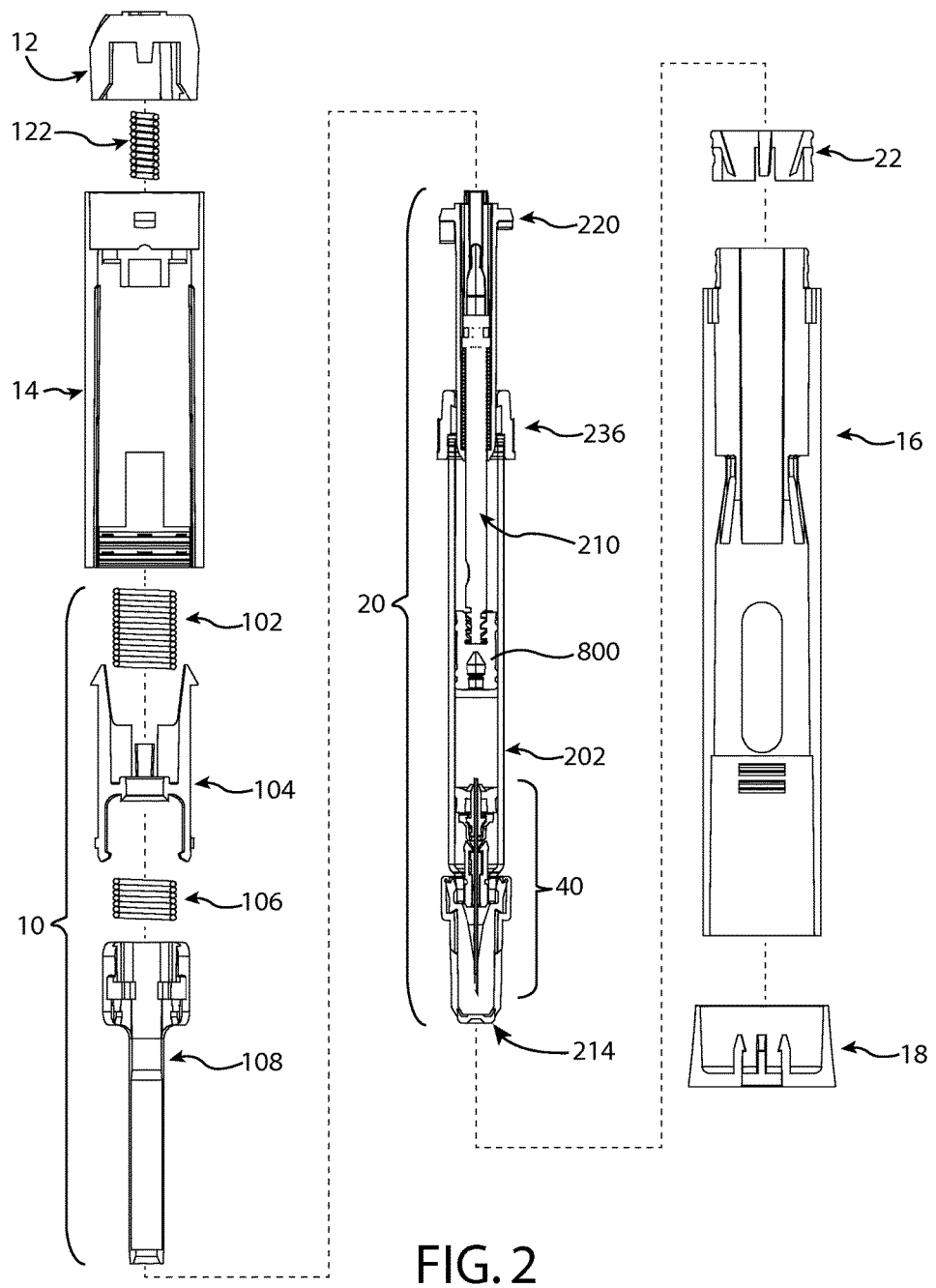
FIG. 2 shows an exploded view of an automatic injector, according to one embodiment of the present invention.

FIG. 1A and FIG. 1B show an embodiment of automatic injector 100 which includes upper housing 14 and lower housing 16. Upper housing 14 and lower housing 16 may be made of any of a number of materials including plastics and glass, but are preferably made of plastic. Upper housing 14 and lower housing 16 may be one unified component consisting of two portions or, as shown in FIGS. 1A and 1B, two separate components. When upper housing 14 and lower housing 16 are two separate components they may be fixedly connected, for example by a glue or adhesive, or removably attached, for example by a screw-fit connection. Automatic injector 100 may also include activation mechanism 12 and cap 18. FIG. 1B shows the interior components of automatic injector 100, i.e., with the upper housing 14 and lower housing 16 hidden from view. As shown in FIG. 1B, automatic injector 100 includes activation mechanism 12, actuation mechanism 10, and syringe cartridge 20 having a plunger 200 (shown in FIG. 4) and needle assembly 40. Cap 18 has been removed for operation of the automatic injector 100 shown in FIG. 1B, but would be removably attached to automatic injector 100 at the distal end D of the device and removed at time of use by the user. FIG. 1B shows the components of actuation mechanism 10 and automatic injector 100, according to at least one embodiment of the present invention, in a locked configuration.

In at least one embodiment, the activation mechanism 12 is a button which may, for example, be rotated to unlock the device and depressed to activate the device, as is detailed further herein. The activation mechanism is shown at proximal end P of automatic injector 100. Typically, drug chamber 222 contains a liquid substance or drug dose for delivery through the needle assembly 40 to a patient. Upon depression, i.e., axial motion in the distal direction, activation mechanism 12 permits actuation mechanism 10 to actuate the needle injection, drug dose delivery, and retraction activation stages of operation. Retraction activation by the actuation mechanism 10 enables retraction of the needle assembly 40 into syringe cartridge barrel 202 and automatic injector 100, as is detailed further herein.

Figures 3A, 3B:
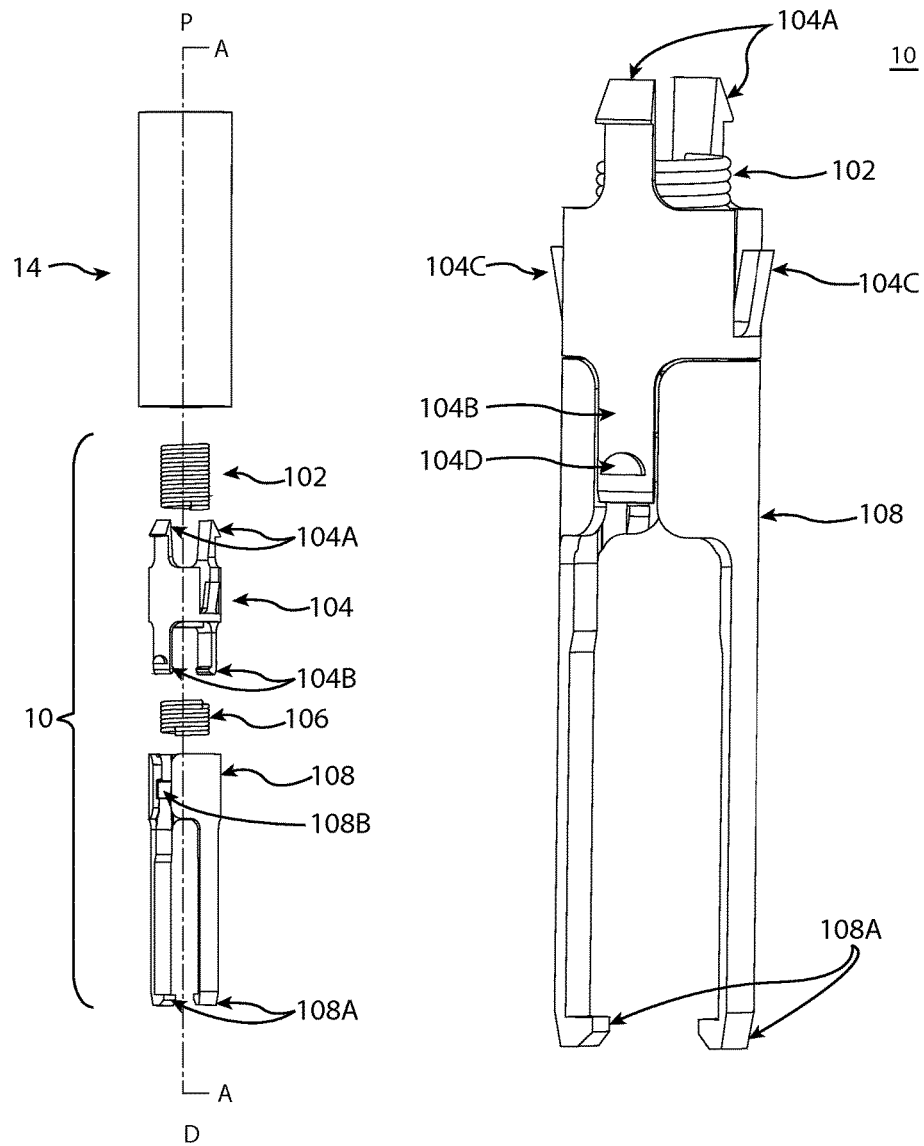
FIG. 3A shows an exploded view of an actuation mechanism for an automatic injector, according to one embodiment of the present invention, which resides substantially within the upper housing when assembled.
FIG. 3B shows an enlarged view of the actuation mechanism shown in FIG. 3A.

FIGS. 3A-3D further detail the actuation mechanism 10, according to at least one embodiment of the present invention, which is a component of the automatic injector. FIG. 3A shows the components of actuation mechanism 10 in an exploded view, in addition to upper housing 14, while FIG. 3B shows these components in a compressed view prior to actuation. In at least one embodiment, actuation mechanism 10 includes first actuation spring 102, first actuation pill 104, second actuation spring 106, and second actuation pill 108. In a compressed configuration prior to actuation, the first actuation spring 102 rests in a compressed, energized state substantially within an upper portion of first actuation pill 104. In this compressed configuration, first actuation pill 104 and second actuation pill 108 are detachably connected, as shown in FIG. 3B, between which second actuation spring 106 resides in a compressed, energized state. Actuation mechanism is maintained in a compressed state by engagement between connector prongs 104B of first actuation pill 104 and connection bridges 108B of second actuation pill 108. The connector prongs 104B and connection bridges 108B are maintained in engagement by interaction between protrusions 104D of first actuation pill 104 and the inner diameter of upper housing 14, as is detailed below. Protrusions 104D may travel within longitudinal channels in the inner diameter of the housing to maintain the rotational alignment of the actuation mechanism. Guide prongs 104C of first actuation pill 104 similarly interface with the inner diameter of the housing to maintain the actuation mechanism 10 in rotational alignment within the automatic injector.

Figures 3C, 3D:
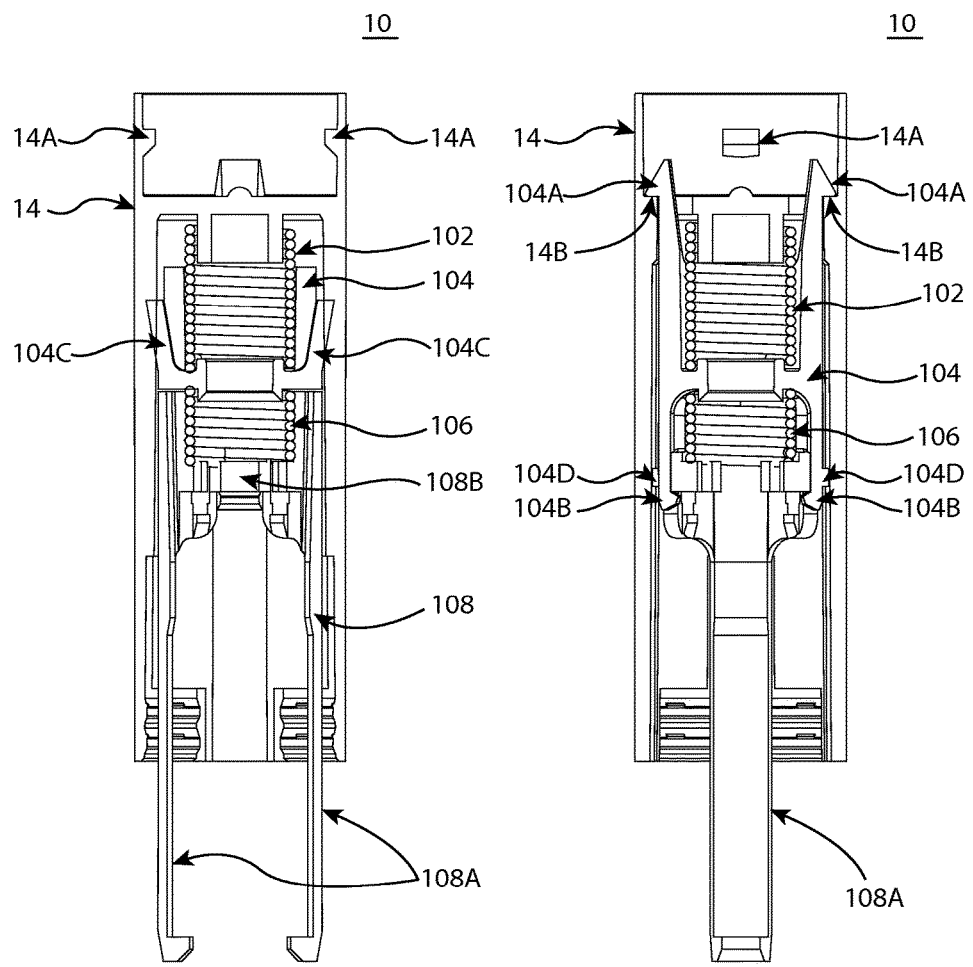
FIG. 3C shows a cross-sectional view of the actuation mechanism shown in FIG. 3A.
FIG. 3D shows a 90 degree rotation of the cross-sectional view shown in FIG. 3C.
Figure 5:
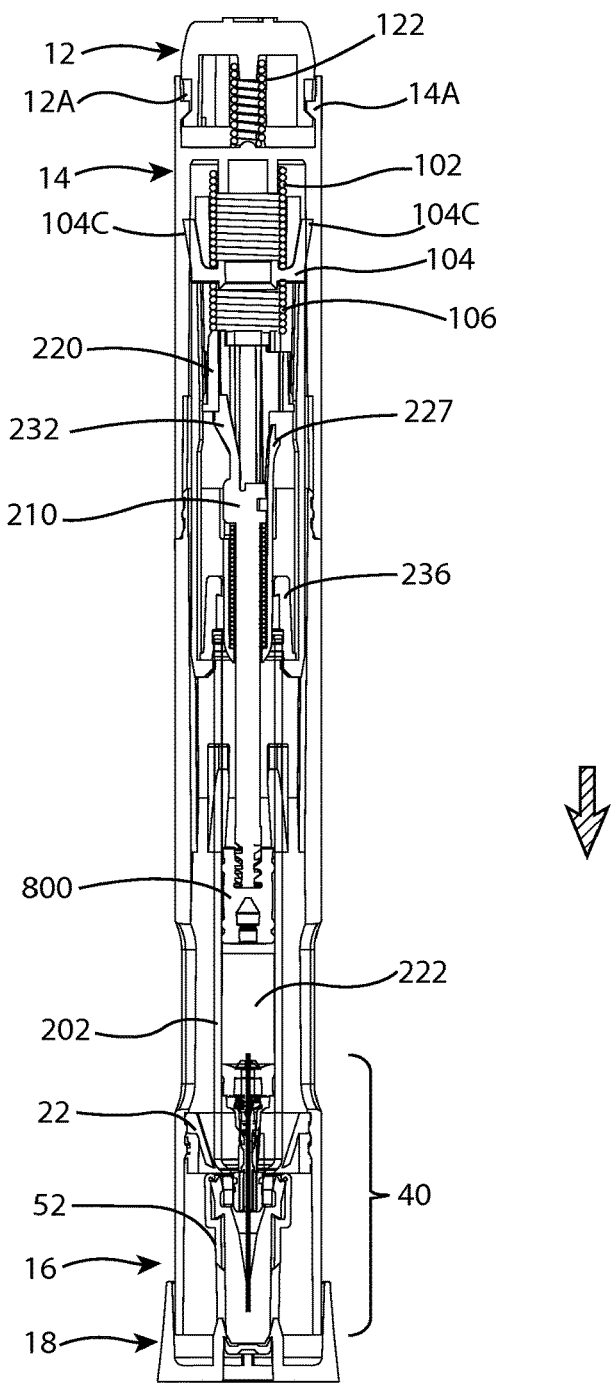
FIG. 5 shows an automatic injector including an actuation mechanism, according to one embodiment of the present invention, in a locked configuration.
Figures 6A, 6B:
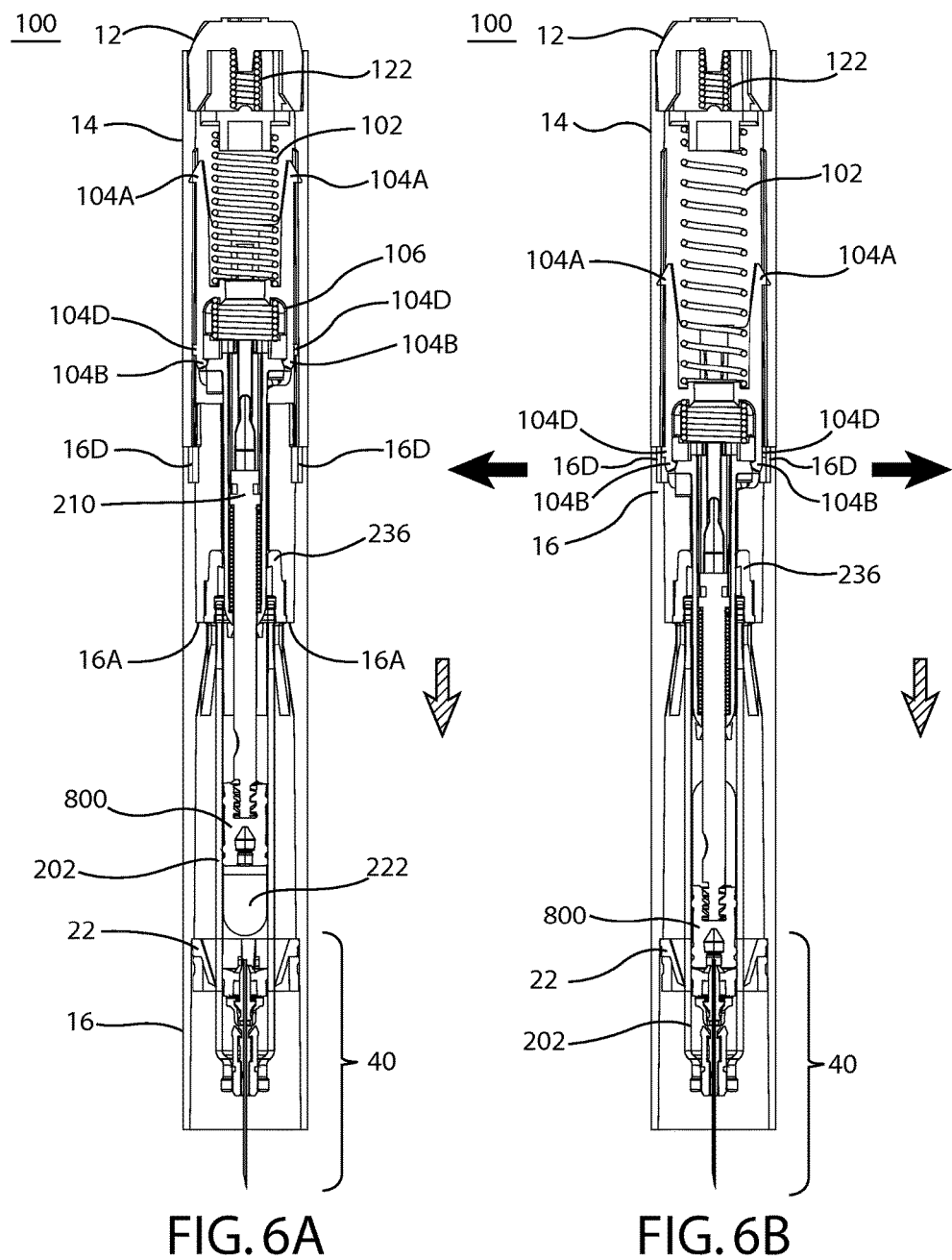
FIG. 6A shows an automatic injector including an actuation mechanism, according to one embodiment of the present invention, in an injection configuration.
FIG. 6B shows an automatic injector including an actuation mechanism, according to one embodiment of the present invention, in a drug dosing configuration.

FIGS. 3C-3D provide cross-sectional views of the actuation mechanism 10 within upper housing 14 prior to activation or actuation of the automatic injector. FIG. 3D shows a 90 degree axial rotation view of the view shown in FIG. 3C. As shown, locking hooks 104A of first actuation pill 104 initially engage locking plateau 14B of upper housing 14. Upon activation of the automatic injector and actuation mechanism by the activation mechanism, locking hooks 104A are caused to move radially inwards and disengage from locking plateau 14B. As would be appreciated by an ordinarily skilled artisan, the term "hooks" is meant to reference any type of engagement mechanism including, for example, prongs, latches, tabs, and the like. Upon such disengagement, first actuation spring 102 is permitted to expand from its compressed, energized state, thereby axially translating first actuation pill 104 in the distal direction. First actuation pill 104 and second actuation pill 108 are retained in engagement during this initial axial translation due to the engagement between connector prongs 104B of first actuation pill 104 and connection bridges 108B of second actuation pill 108 described above. Such operation of the actuation mechanism 10 is also shown in FIGS. 5, 6A, and 6B, in which actuation mechanism 10 is incorporated into an automatic injector 100. As shown in FIG. 5, retention prongs 108A of second actuation pill 108 are initially used to engage bottom of release ring 236 to maintain the position of the syringe cartridge and needle assembly within the housing during, for example, removal of the needle shield. The retention prongs 108A may also be used to brace against barrel 202 of syringe cartridge 20 to ensure substantially axial alignment of these components during storage, transport, and operation of the actuation mechanism and automatic injector. Support ring 22 may similarly be utilized to ensure substantially axial alignment of the components.

Referring now to FIGS. 5-8, expansion of the first actuation spring 102 and the resulting axial translation of the actuation mechanism 10 in the distal direction causes exposure of the needle assembly 40 from the distal end of the automatic injector, such as for injection of a needle into a user. This is evident in the transition of components shown in FIGS. 5, 6A, and 6B. The axial translation of the actuation mechanism in the distal direction causes plunger 200 to also move in the distal direction, while syringe cartridge is held substantially in place by engagement between release ring 236 and lower housing plateaus 16A. Lower housing plateaus 16A may also be located at various positions within the lower housing to limit the depth of needle insertion. Distal translation of the plunger 200 within barrel 202 of syringe cartridge 20 forces a liquid, such as a drug treatment, from drug chamber 222 through needle assembly 40 and into a user for drug delivery, as is detailed further below. As such, expansion of the first actuation spring 102 initially drives insertion of the needle into the patient to a desired depth specified by the location of the lower housing plateaus 16A within the housing. Upon interaction between release ring 236 and lower housing plateaus 16A to block further travel of the syringe cartridge, the continued expansion of the first actuation spring 102 proceeds to translate plunger 200 within barrel 202 to deliver the drug dose.

Figure 4:
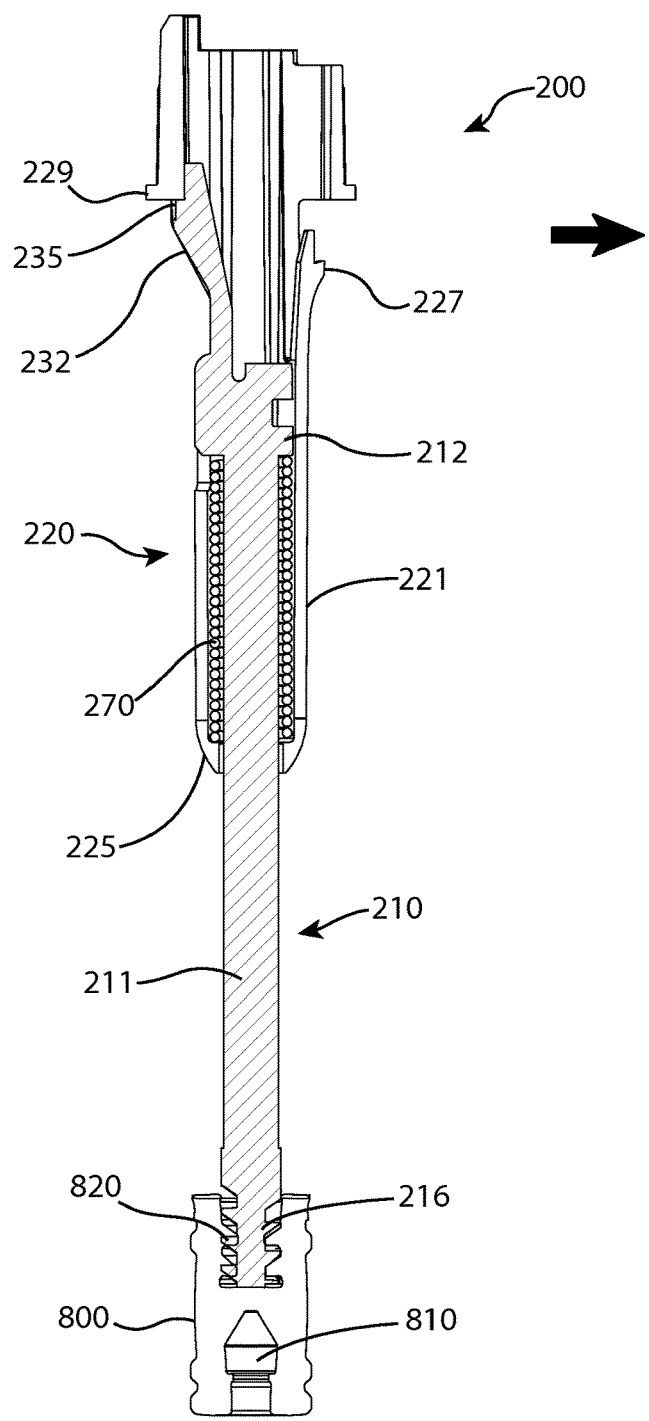
FIG. 4 shows a cross-sectional view of a plunger of a retractable syringe component of an automatic injector, according to one embodiment of the present invention.

Referring now to FIG. 4, plunger 200 comprises plunger inner 210 comprising shaft 211, arm 232, annular ledge 212 and seal-engaging member 216, which in this embodiment is a screw threaded projection at the distal end of plunger 200, which engages complementary, screw-threaded recess 820 of plunger seal 800. Plunger seal 800 further comprises needle-engaging portion 810. Plunger 200 further comprises plunger outer 220 having elongate body 221 with base 225 and locking member 227. Plunger 200 further comprises plunger spring 270 which is mounted between plunger inner 210 and plunger outer 220, held in an initially compressed state between ledge 212 of plunger inner 210 and base 225 of plunger outer 220. Initially, ledge 235 of arm 232 abuts rim 229 of plunger outer 220 to prevent axial movement of plunger inner 210 relative to plunger outer 220. However, arm 232 of plunger inner 210 is resiliently flexible and movable in the direction of the solid arrow shown in FIG. 4, which will allow disengagement of plunger inner 210 from plunger outer 220 to facilitate decompression of plunger spring 270, as will be described hereinafter.

Figure 8:
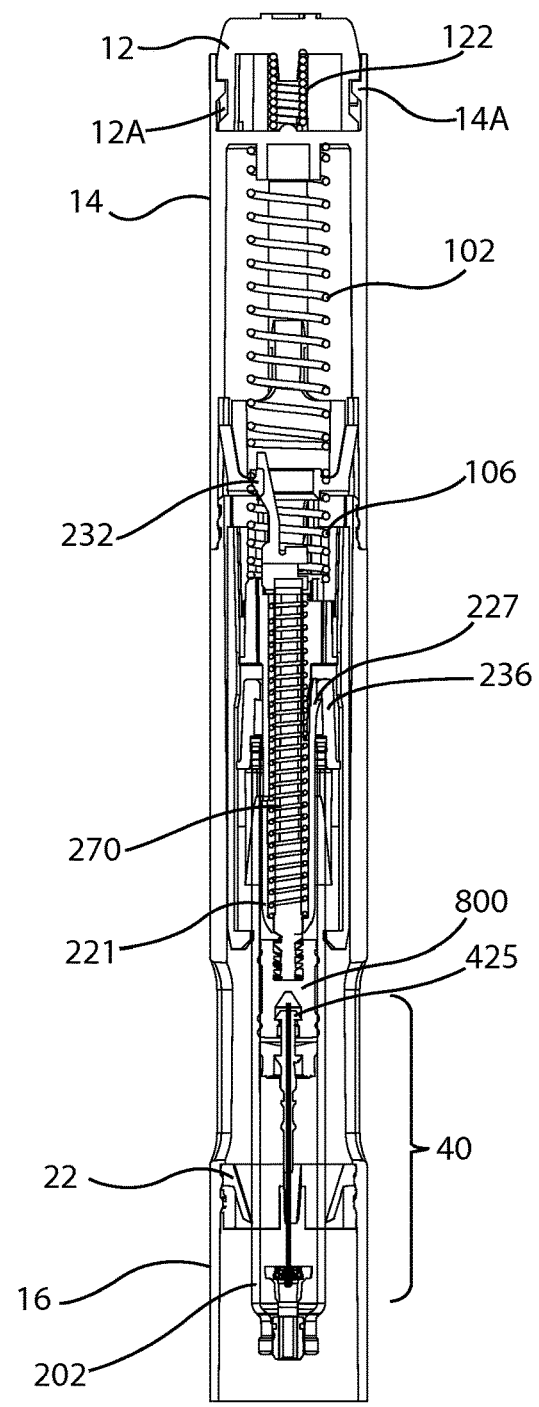
FIG. 8 shows an automatic injector including an actuation mechanism, according to one embodiment of the present invention, in a refraction completed configuration.
Figure 9:
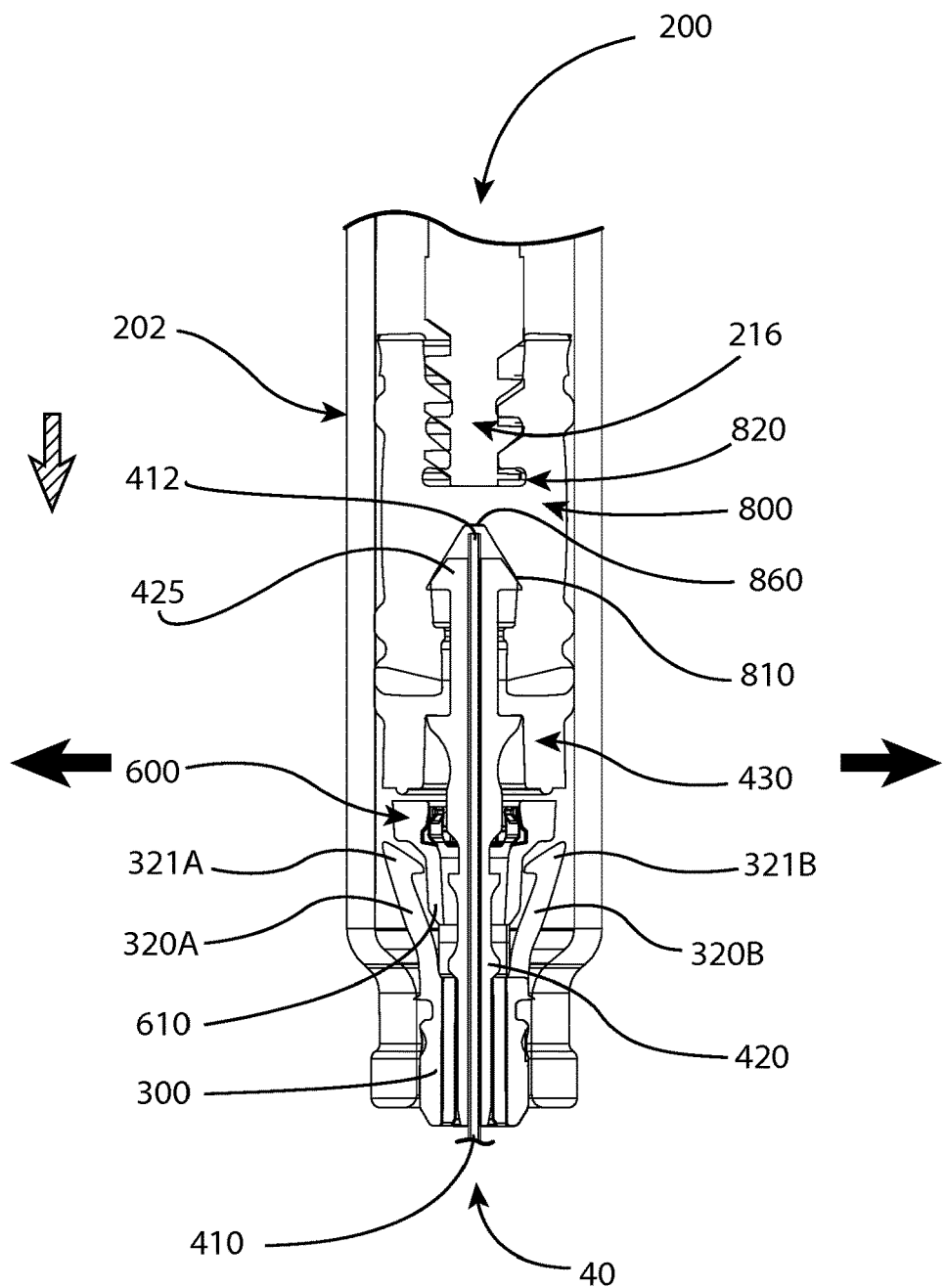
FIG. 9 shows an embodiment of a needle assembly engaged by a plunger prior to retraction.

Referring now to FIG. 9, needle assembly 40 includes cannula 410, needle body 420, retainer 300, needle seal 430 and ejector 600. The needle assembly 40 is mounted into the distal end of barrel 202 of the syringe cartridge. FIG. 9 shows the components in the retraction activation stage, when contact between plunger seal 800 and needle seal 430, needle seal 430 and ejector 600, and ejector 600 and arms 320A, B of retainer 300 cause hook-ends 321A, B of retainer 300 to disengage from needle body 420 for retraction of needle assembly 40. Cannula 410 may be a number of fluid tubes but is preferably a rigid needle, such as a rigid steel needle. Prior to or upon retraction activation, plunger recess 860 of plunger seal 800 engages proximal segment 425 of needle body 420 for refraction of needle assembly 40. The retraction activation stage is detailed further with reference to the operation of automatic injector 100 in FIGS. 5-8 hereinafter.

Operation of actuation mechanism 10 and automatic injector 100 will be described with particular reference to FIGS. 1-3 and 5-8. In these embodiments, drug chamber 222 of barrel 202 contains a fluid suitable for injection into a user. As evident in FIG. 5, safety cap 18 (shown also in FIG. 1A) has been removed from lower housing 16 to allow activation of the device, injection of the needle assembly, and drug delivery. Initially, activation mechanism 12 is in a locked configuration enabled by the releasable engagement between locking prongs 14A of upper housing 14 and locking grooves 12A of activation mechanism 12. Locking grooves 12A may be channels, detents, or the like along the radial circumference of the activation mechanism, as shown in FIG. 1B, within which locking prongs 14A may travel. Initially, the locking prongs 14A are in a position within the locking grooves 12A which prevents depression of the activation mechanism 12. The activation mechanism 12 may be rotated around the longitudinal axis to an unlocked position, where the locking prongs 14A are aligned with a portion of the locking grooves 12A that permits axial depression of the activation mechanism 12. Optionally, an activation spring 122 may be retained within the activation mechanism 12, between the activation mechanism and the proximal end of the upper housing 14, for example to maintain the activation mechanism 12 in a locked position until user operation and to provide the user tactile resistance upon activation. This provides useful user feedback to ensure that the proper injection procedures are followed with the device and that removal of the cap is completed prior to injection.

In the configurations shown in FIG. 3D and FIG. 5, locking hooks 104A of first actuation pill 104 initially engage locking plateau 14B of upper housing 14. After removal of the cap and unlocking of the activation mechanism, such as by axial rotation of the activation mechanism, the device may be placed in contact with the target location of the user and activated for injection, drug delivery, and needle retraction. Upon activation of the automatic injector and actuation mechanism by the activation mechanism, locking hooks 104A are caused to move radially inwards and disengage from locking plateau 14B. Upon such disengagement, first actuation spring 102 is permitted to expand from its compressed, energized state, thereby axially translating first actuation pill 104 in the distal direction. First actuation pill 104 and second actuation pill 108 are retained in engagement during this initial axial translation due to the engagement between connector prongs 104B of first actuation pill 104 and connection bridges 108B of second actuation pill 108 described above. This stage initiates needle insertion into the patient and begins drug delivery to the patient.

FIGS. 6A and 6B show the automatic injector, in a cross-sectional view that is 90 degrees rotated around the axis from the view shown in FIG. 5, after the device has been activated. As the first actuation spring 102 continues to expand from its compressed, energized state, it causes axial translation of the actuation mechanism in the distal direction. This action of the actuation mechanism forces plunger 200 to also move in the distal direction (in the direction shown by the hatched arrow), while syringe cartridge 20 is held substantially in place by engagement between release ring 236 and lower housing plateaus 16A. Lower housing plateaus 16A may also be located at various positions within the lower housing to limit the depth of needle insertion. Distal translation of the plunger 200 within barrel 202 of syringe cartridge 20 forces a liquid, such as a drug treatment, from drug chamber 222 through needle assembly 40 and into a user for drug delivery. The dimensions of the components and the lengths of axial travel within the device are configured such that protrusions 104D of first actuation pill 104 reach interior recesses 16D of lower housing 16 just prior to, or substantially at the same time as, plunger seal 800 contacting the needle seal of needle assembly 40, effectively ensuring that the recess of needle seal 430 has engagedly captured segment 425 of the needle body of the needle assembly 40 for retraction and prior to activation of the retraction mechanism. Alternatively, interior recesses may be dimensioned and located at various points in the upper housing, or within a unified housing body, yet function in the same manner as described in the embodiment shown in FIGS. 6A and 6B. Similarly, interior recesses may be changes in inner diameter between the upper and lower housings. At this stage, protrusions 104D of first actuation pill 104 are permitted to spring radially outwards into interior recesses 16D of lower housing 16 (in the directions shown by the solid arrows in FIG. 3B). This action enables connector prongs 104B of first actuation pill 104 to disengage from connection bridges 108B of second actuation pill 108, thereby actuating the function of the second actuation pill.

Figure 7:
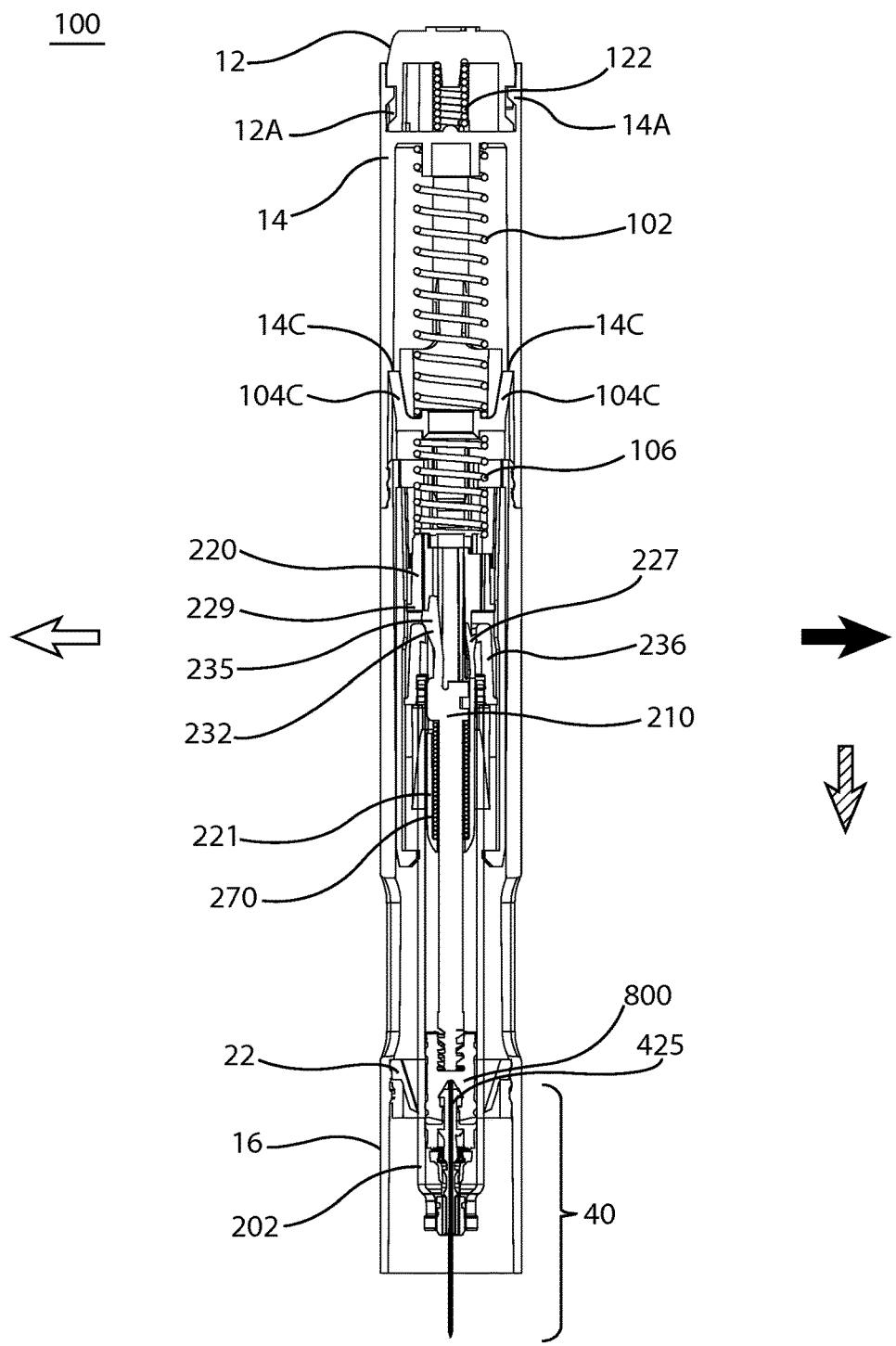
FIG. 7 shows an automatic injector including an actuation mechanism, according to one embodiment of the present invention, in a refraction activated configuration.

FIG. 7 shows the automatic injector, in the same cross-sectional viewing angle as FIG. 5, as the second actuation pill is actuated. As described above, upon release of the connector prongs 104B of first actuation pill 104 from their engagement with connection bridges 108B of second actuation pill 108, second actuation spring 106 is permitted to expand from its compressed, energized state, thereby driving the plunger further in the distal direction. Second actuation spring 106 is prevented from driving the first actuation pill in the proximal direction by surface interaction between guide prongs 104C of the first actuation pill and lockout notches 14C of upper housing 14. This configuration ensures that substantially all of the energy stored in the second actuation spring 106 is released in the distal direction. The second actuation pill 108 functions to ensure that all of the drug treatment is delivered to the user and to activate the needle retraction mechanism.

In at least one embodiment of the present invention, the needle retraction is essentially similar to that described in WO2011/075760, and will be briefly described as follows with reference to FIGS. 7-11. During delivery of fluid contents, plunger 200 moves axially through barrel 202 in the direction of the hatched arrow in FIG. 7. As shown in FIG. 9, plunger seal 800 bears against needle seal 430, which in turn bears against ejector 600. Further to this, ejector ring 610 moves hook-ends 321A, B of arms 320A, B of retainer 300 radially outwardly in the direction of the solid arrows in FIG. 9, thereby disengaging needle body 420 from retainer 300 to release needle body 420 and cannula 410 for subsequent retraction. At this point, recessed seat 810 of plunger seal 800 has engaged segment 425 of retractable needle body 420 and recess 860 has received fluid end 412 of cannula 410. This effectively couples needle body 420 and cannula 410 to plunger inner 210 since plunger inner 210 is connected to the proximal end of plunger seal 800.

Figure 10:
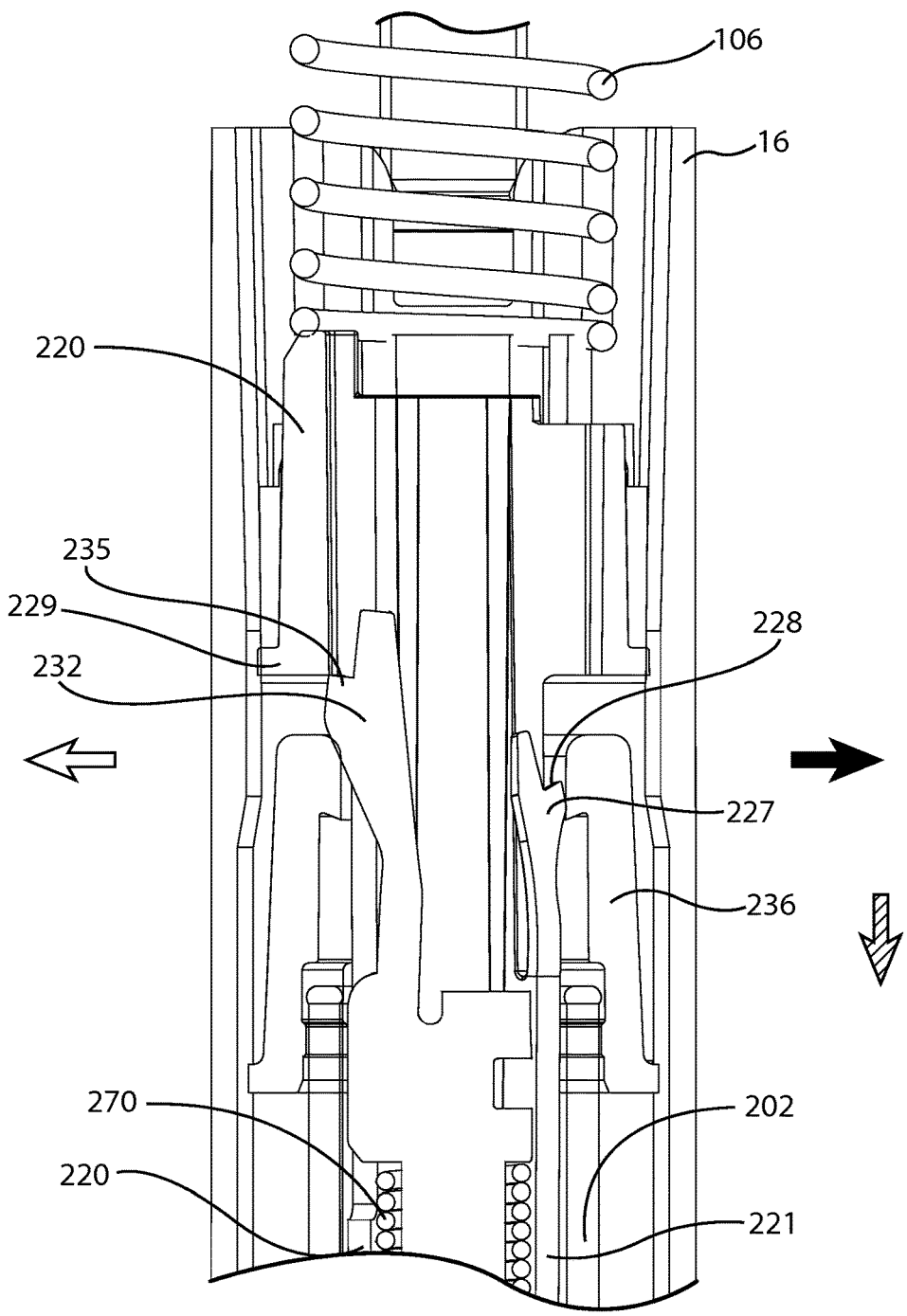
FIG. 10 shows an enlarged view of the retraction activated configuration shown in FIG. 7, in which an embodiment of a release ring disengages a plunger inner from a plunger outer to facilitate spring decompression and needle retraction.
Figure 11:
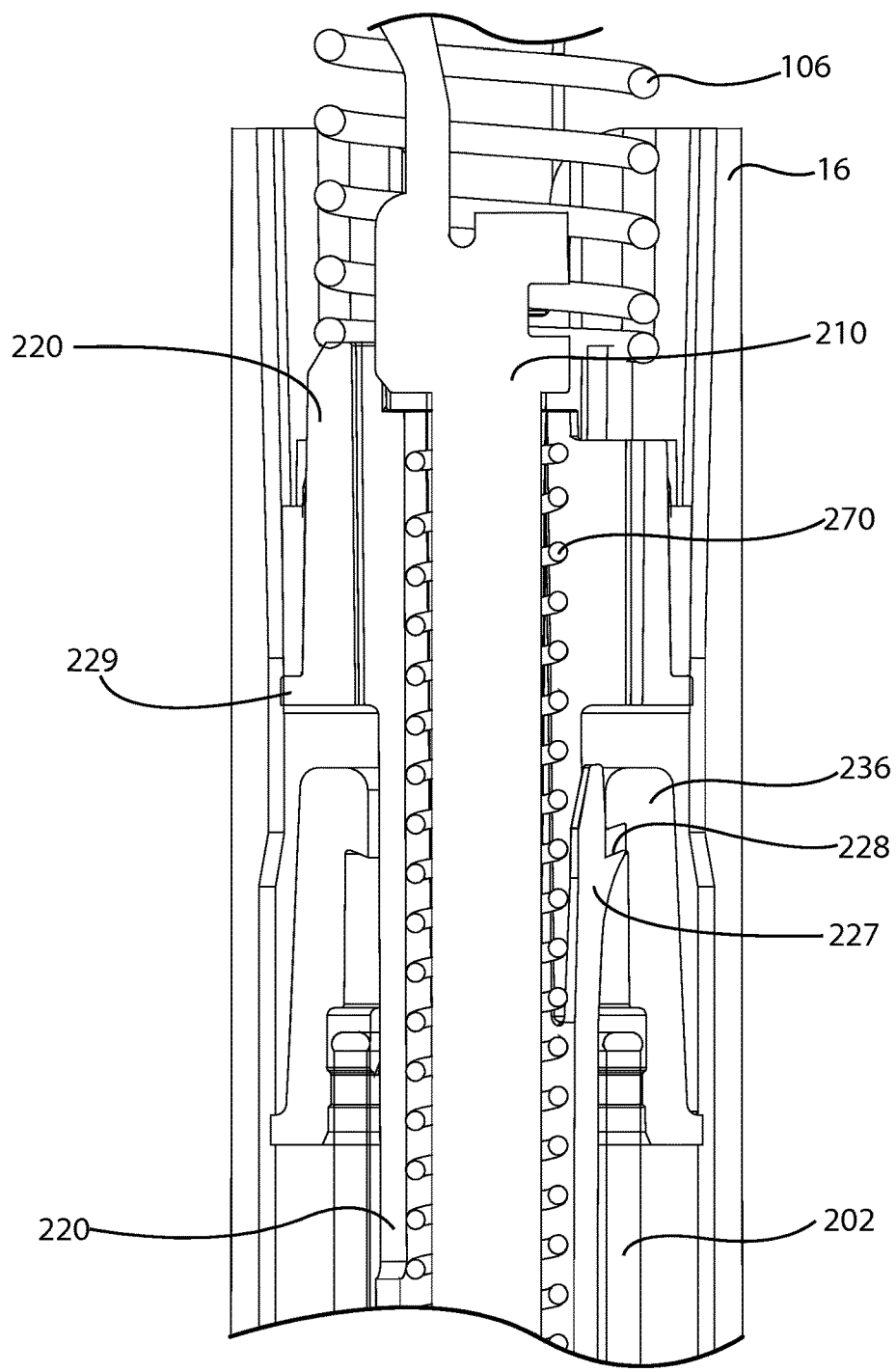
FIG. 11 shows an enlarged view of the retraction completed configuration shown in FIG. 8.

As shown in FIG. 7 and FIG. 10, in order for needle body 420 and cannula 410 to retract at the end of delivery of fluid contents, compressed spring 270 must decompress, which is facilitated by plunger inner 210 disengaging from plunger outer 220. This disengagement is facilitated by release ring 236. As plunger inner 210 and plunger outer 220 are substantially fully depressed (i.e., axially translated in the distal direction as per the hatched arrow) to inject fluid from barrel 202, one or both may contact release ring 236. Through this contact, release ring 236 moves arm 232 radially inwardly (in the direction of the solid arrow) and out of engagement with rim 229 of plunger outer 220. This disengagement allows compressed spring 270 to decompress and push against ledge 212 (shown in FIG. 4 and FIG. 7) of plunger inner 210 to thereby retract plunger inner 210 with plunger seal 800, needle body 420, and cannula 410 coupled thereto. Plunger outer 220 remains substantially in contact or connection with release ring 236, while plunger inner 210 coupled to needle body 420 and cannula 410 is axially translated in the proximal direction by decompression of spring 270, thereby retracting cannula 410 and needle body 420. FIG. 8 and FIG. 11 show the components of the automatic injector after needle retraction has completed. At this stage, cannula 410 is fully retracted into the housing and/or barrel 202. This needle or cannula retraction is highly desirable as it provides integrated safety features while simultaneously providing a true end of dose indication to the user.

Suitably, automatic injector 100 provides one or more locking systems for plunger 200. As shown in FIGS. 7, 8, and 11, in one embodiment of said locking system, plunger outer 220 of plunger 200 includes locking member 227 having edge 228 which engages underside 237 of release ring 236 after needle retraction. This engagement prevents or impedes further movement of plunger 200 relative to the release ring 236 in the proximal direction, as shown in FIG. 11, while plunger inner 210 is permitted to move in the proximal direction. Accordingly, in addition to initially assisting in the activation of needle retraction, the release ring 236 may secondarily function to lock plunger 200 after initial use to thereby prevent re-use. As stated above, the force of the second actuation spring acting upon the plunger outer itself may additionally or alternatively prevent or "lock-out" the plunger outer from axial travel in the proximal direction after actuation.

Certain optional standard components or variations of automatic injector 100 are contemplated while remaining within the breadth and scope of the present invention. For example, upper or lower housings may optionally contain one or more transparent or translucent windows 50, as shown in FIG. 1, to enable the user to view the operation of the automatic injector or verify that drug dose has completed. Additionally, an optional needle shield 52 may be utilized, as shown in FIG. 5, to protect cannula 410. The needle shield 52 may be connected, for example, to cap 18 and removed prior to operation of the automatic injector 100. Similarly, one or more of the components of actuation mechanism 10 and automatic injector 100 may be modified while remaining functionally within the breadth and scope of the present invention. For example, as described above, while the housing of automatic injector 100 is shown as two separate components upper housing 14 and lower housing 16, these components may be a single unified component. Similarly, while support ring 22 is shown as a separate bracing component, it may be a pre-formed aspect on the inner diameter of the housing. Such standard components and functional variations would be appreciated by one having ordinary skill in the art and are, accordingly, within the breadth and scope of the present invention. It will be appreciated from the foregoing that the actuation mechanisms and automatic injectors disclosed herein provide an efficient and easily-operated system for automated drug delivery from a drug container, with integrated safety features and true end of dose indication to the user.

Assembly and/or manufacturing of actuation mechanism 10, automatic injector 100, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization fluids and processes may be employed during the manufacture of the novel components and devices. Furthermore, known sterilization processes may be employed at one or more of the manufacturing or assembly stages to ensure the sterility of the final product.

The automatic injector may be assembled in a number of methodologies. In one method, the second actuation spring is first compressed between a first actuation pill and a second actuation pill. The second actuation spring may be locked in a compressed, energized state by detachably engaging one or more connector prongs of the first actuation pill with one or more respective connection bridges of second actuation pill. A first actuation spring may subsequently be inserted into a housing and compressed between the housing and the first actuation pill by detachably engaging one or more locking hooks of the first actuation pill with a locking plateau of the housing. In this configuration, wherein the first actuation spring is initially maintained in a compressed, energized state substantially within an upper portion of the first actuation pill. A syringe cartridge comprising a plunger and a needle assembly may be inserted into the housing such that a proximal end of the plunger contacts the second actuation pill. Alternatively, the syringe cartridge, or components thereof including the plunger, may be connected to the second actuation pill prior to insertion of the components into the housing. For example, the proximal end of the plunger outer may interface with one or more engagement features within the second actuation pill. This enables, for example, rotational alignment of the plunger, prevents shifting of the plunger from a substantially axial alignment, and helps ensure an even distribution of force onto the plunger upon actuation of the first and second actuation pills. The syringe cartridge may be a number of syringes such as, for example, a prefilled syringe containing a drug treatment. Preferably, the syringe is a prefilled retractable syringe, as described above. The method may further include the step of: attaching an activation mechanism to the housing, wherein the activation mechanism is configured to contact the one or more locking hooks of the first actuation pill upon activation. The activation mechanism may be positioned such that it is in a locked configuration for, for example, shipping and storage of the automatic injector. Additionally, the method may include the step of attaching a cap having a needle shield aspect, or attaching separate cap and needle shield, to the distal end of the syringe cartridge and automatic injector. When the cap and needle shield are separate components, the support ring may be utilized to brace the proximal end of the needle shield during attachment of the cap. This also helps to prevent pressurization of the syringe cartridge during assembly.

As discussed above, a glue or adhesive may be utilized to affix one or more components of the actuation mechanism and/or automatic injector to each other. Alternatively, one or more components of the actuation mechanism and/or automatic injector may be a unified component. For example, the upper housing and lower housing may be separate components affixed together by a glue or adhesive, a screw fit connection, an interference fit, and the like; or the upper housing and lower housing may be a single unified component. These components may be sterilized individually or together, and may be assembled in a sterile environment or sterilized after assembly. Similarly, the assembly of the embodiments of the present invention may utilize a number of other standard manufacturing practices.

The automatic injector may be utilized in a number of different ways. For example, in one embodiment the method of operating an automatic injector includes the step of: (i) disengaging one or more locking hooks of a first actuation pill from a locking plateau of a housing, wherein such disengagement permits a first actuation spring to expand substantially along a longitudinal axis of the housing from its initial energized state. The expansion of the first actuation spring translates the actuation mechanism substantially along an axis of the automatic injector in the distal direction. As the first actuation pill reaches one or more recesses in the inner surface of the housing, the first actuation pill is permitted to disengage from the second actuation pill. In a preferred embodiment, this disengagement occurs when one or more connector prongs of the first actuation pill disconnect from corresponding connection bridges of the second actuation pill. This disconnection permits a second actuation spring to expand substantially along the longitudinal axis of the housing from its initial energized state.

Protrusions on the connector prongs of the first actuation pill may be utilized to bias the connector prongs into engagement with the connection bridges when in the connected stage. Such protrusions may be permitted to expand into the recesses of the inner surface of housing as the actuation mechanism reaches the recesses, thereby permitting disconnection between the one or more connector prongs of the first actuation pill and the corresponding connection bridges of the second actuation pill. The actuation mechanism may initially drive the needle injection and drug delivery into the patient. Subsequently, the actuation mechanism may activate the retraction mechanism of the syringe cartridge, as described above. The method may further include the steps of: operating the plunger of the automatic injector to deliver a substance to a recipient. Prior to step (i), the method may further include the step of: unlocking an activation mechanism and activating the activation mechanism, as described above.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

What is claimed is:

1. An actuation mechanism for an automatic injector, comprising: a first actuation spring, a first actuation pill, a second actuation spring arranged distal to and coaxially with the first actuation spring and a second actuation pill, wherein in an initial configuration the first actuation spring resides in a compressed, energized state substantially within an upper portion of the first actuation pill, and the second actuation spring resides in a compressed, energized state between the first actuation pill and the second actuation pill, and the first actuation pill and the second actuation pill are detachably, directly connected to prevent relative movement between the first actuation pill and the second actuation pill and to maintain the second actuation spring in the compressed, energized state between the first actuation pill and the second actuation pill.

2. The actuation mechanism of claim 1, wherein the first actuation pill and the second actuation pill are detachably, directly connected by engagement between one or more connector prongs of the first actuation pill and one or more respective connection bridges of the second actuation pill.

3. The actuation mechanism of claim 2, wherein the one or more connector prongs of the first actuation pill each have protrusions which extend outwards from the first actuation pill.

4. The actuation mechanism of claim 1, wherein the first actuation pill has one or more locking hooks at a proximal end of the first actuation pill.

5. The actuation mechanism of claim 1, wherein the second actuation pill has one or more retention prongs at a distal end of the second actuation pill.

6. The actuation mechanism of claim 1, wherein the first actuation pill has one or more guide prongs extending outwards from the first actuation pill.

7. The actuation mechanism of claim 1, wherein the first actuation pill and second actuation pill are substantially cylindrical.

8. An automatic injector comprising a housing, an activation mechanism, an actuation mechanism, and a syringe cartridge having a plunger and a needle assembly, wherein the actuation mechanism comprises: a first actuation spring, a first actuation pill, a second actuation spring arranged distal to and coaxially with the first actuation spring and a second actuation pill, wherein in an initial configuration the first actuation spring resides in a compressed, energized state substantially within an upper portion of the first actuation pill, and the second actuation spring resides in a compressed, energized state between the first actuation pill and the second actuation pill, and the first actuation pill and the second actuation pill are detachably, directly connected to prevent relative movement between the first actuation pill and the second actuation pill and to maintain the second actuation spring in the compressed, energized state between the first actuation pill and the second actuation pill.

9. The automatic injector of claim 8, wherein the housing comprises an upper housing and a lower housing, and wherein the upper housing, the lower housing, the first actuation pill, and the second actuation pill are substantially cylindrical.

10. The automatic injector of claim 8, wherein the first actuation pill has one or more locking hooks at a proximal end of the first actuation pill which initially engage a locking plateau at an interior proximal end of the housing.

11. The automatic injector of claim 10, wherein the activation mechanism is capable of engaging the one or more locking hooks of the first actuation pill to disengage the locking hooks from the locking plateau of the housing.

12. The automatic injector of claim 8, wherein the first actuation pill and the second actuation pill reside within the housing and are detachably, directly connected with each other by engagement between one or more connector prongs of the first actuation pill and one or more respective connection bridges of the second actuation pill.

13. The automatic injector of claim 12, wherein the one or more connector prongs each have protrusions which interface with longitudinal channels along an inner surface of the housing.

14. An automatic injector comprising
- a housing having an inner surface, and including longitudinal channels and one or more recesses along the inner surface,
- a syringe cartridge having a plunger and a needle assembly,
- an activation mechanism, and
- an actuation mechanism, the actuation mechanism including
  - a first actuation pill residing in the housing and including one or more connector prongs, the one or more connector prongs each having protrusions which interface with the longitudinal channels along the inner surface of the housing,
  - a first actuation spring, the first actuation spring residing, in an initial configuration, in a compressed, energized state substantially within an upper portion of the first actuation pill,
  - a second actuation spring, the second actuation spring residing, in the intial configuration, in a compressed, energized state between the first actuation pill and the second actuation pill, and
  - a second actuation pill residing in the housing and including one or more connection bridges,
- wherein, in the initial configuration, the first actuation pill and the second actuation pill are detachably, directly connected to prevent relative movement between the first actuation pill and the second actuation pill and to maintain the second actuation spring in the compressed, energized state between the first actuation pill and the second actuation pill, the first actuation pill and the second actuation pill being detachably, directly connected with each other by engagement between the one or more connector prongs of the first actuation pill and the respective one or more connection bridges of the second actuation pill,
- the protrusions of the connector prongs being adapted to interface with and expand into the recesses of the housing to permit the one or more connector prongs of the first actuation pill to disengage from the respective one or more connection bridges of the second actuation pill.

* * * * *

UNITED STATES PATENT AND TRADEMARK OFFICE
CERTIFICATE OF CORRECTION

PATENT NO. : 10,166,336 B2
APPLICATION NO. : 14/328914
DATED : January 1, 2019
INVENTOR(S) : Katlin M. Lumme et al.

Page 1 of 1

It is certified that error appears in the above-identified patent and that said Letters Patent is hereby corrected as shown below:

On the Title Page

Item (63) Related U.S. Application Data, delete "Aug. 3, 2012" and insert -- Aug. 23, 2012 --.

In the Claims

In Claim 1, Column 14, Line 14, delete "in the compressed," and insert -- in a compressed, --.

In Claim 8, Column 14, Line 53, delete "in the compressed," and insert -- in a compressed, --.

In Claim 14, Column 16, Line 2, delete "intial" and insert -- initial --.

Signed and Sealed this
Ninth Day of April, 2019

Andrei Iancu
*Director of the United States Patent and Trademark Office*